(12) United States Patent
Farache

(10) Patent No.: US 9,091,867 B1
(45) Date of Patent: Jul. 28, 2015

(54) SYSTEM, METHOD AND DEVICE FOR MEASURING PUPILLARY DISTANCE

(71) Applicant: Fortunato Farache, Doral, FL (US)

(72) Inventor: Fortunato Farache, Doral, FL (US)

(*) Notice: Subject to any disclaimer, the term of this patent is extended or adjusted under 35 U.S.C. 154(b) by 0 days.

(21) Appl. No.: 14/593,908

(22) Filed: Jan. 9, 2015

Related U.S. Application Data

(60) Provisional application No. 62/066,900, filed on Oct. 22, 2014.

(51) Int. Cl.
*A61B 3/10* (2006.01)
*G02C 13/00* (2006.01)
*A61B 3/11* (2006.01)

(52) U.S. Cl.
CPC .............. *G02C 13/005* (2013.01); *A61B 3/111* (2013.01)

(58) Field of Classification Search
CPC ................................ A61B 3/111; A61B 3/112
USPC ...................... 351/204, 246, 200; 33/200, 28; 345/629, 632
See application file for complete search history.

(56) References Cited

U.S. PATENT DOCUMENTS

| 5,617,155 | A | 4/1997 | Ducarouge et al. |
| 6,095,650 | A | 8/2000 | Gao et al. |
| 6,535,223 | B1 * | 3/2003 | Foley .............................. 345/629 |
| 7,274,806 | B2 | 9/2007 | Fukuma et al. |
| 7,628,487 | B2 * | 12/2009 | Moinard ........................ 351/178 |
| 7,665,843 | B2 | 2/2010 | Xie |
| 8,459,792 | B2 | 6/2013 | Wilson et al. |

FOREIGN PATENT DOCUMENTS

| EP | 0680722 A1 | 11/1995 |
| EP | 0680722 B1 | 12/1997 |

* cited by examiner

*Primary Examiner* — Hung Dang

(57) ABSTRACT

A measuring system that embodies a method and a calibration frame for use in measuring pupillary distances and segment heights is provided. The method includes an individual choosing a desired frame and then receiving a calibrated frame that substantially matches the shape and size of the desired frame. The calibrated frame also provides known measurements over its vertical plane between selected points. The method includes a photographed image of the calibrated frame worn by the individual so that using the known measurements of the calibrated frame to compare to the corresponding distance measured off the photographed image, the pupillary distances and segment heights can be determined for providing prescription lens for the desired frame, including multifocal (progressive) eyeglasses and bi-focal eyeglasses. Thereby the measuring of pupillary distances and segment heights takes into account relevant physiognomy and the desired frame of the measured individual, and so facilitating online purchases of prescription frames.

23 Claims, 4 Drawing Sheets

SYSTEM, METHOD AND DEVICE FOR MEASURING PUPILLARY DISTANCE

CROSS-REFERENCE TO RELATED APPLICATION

This application claims the benefit of priority of U.S. provisional application number 62/066,900, filed 22 Oct. 2014, the contents of which are herein incorporated by reference.

BACKGROUND OF THE INVENTION

The present invention relates to pupillary measurements and, more particularly, to a system, method and device for measuring pupillary distance, taking into account relevant physiognomy and the desired frame of the measured individual, and so facilitating online purchases of prescription frames.

Traditionally, measuring pupillary distance required an individual to utilize the services of an optician using a ruler or specialized equipment, usually by visiting an optical store, to obtain such measurements. Such measurements include pupillary distances and segment heights, wherein the pupillary distances are the horizontal distance between each eye-pupil and the center of the frame nose-bridge (always necessary to make eyeglasses), and wherein the segment heights (not required for single vision eyeglasses) are the vertical distances (for progressive eyeglasses) between each eye-pupil, and (for bi-focal eyeglasses) between each top of the eye's lower eye-lid, and their corresponding eye-frame.

In-store measurements were the norm because even small pupillary measurement error can make prescription eyeglasses exhibit prismatic behavior, causing squint, headaches, and dizziness. The importance of centering an optical lens in alignment with the individual's eye pupil is one of the key factors for making prescription eyeglasses successfully.

Recently, methods of measuring pupillary distance have been developed so the individual need not employ the services of an optician—i.e., remote methods. One popular method only suitable for single-vision eyeglasses consists on taking a picture of the individual while placing the back-side of a credit card, a CD/DVD or an object of a commonly known length on his/her chin in order to be able to obtain the scale of the picture and calculate the inter-pupillary distance from the picture. However, this method is not suitable for, among other things, multifocal (progressive) eyeglasses because it does not account for the desired frame the individual wants to wear, leaving the segment heights unknown relative to the position of the desired frame seated on the individual's nose. This method is also not suitable for an individual with an asymmetrical face, as the actual pupillary distances from the nose to their corresponding right and left eyes may differ from the value obtained from a single inter-pupillary measurement. Moreover, this method may also requires the individual to get assistance of another person to take the picture; otherwise risk the pupillary measurement error(s) and its associated effects mentioned above.

Another popular remote method consists on having the individual taking his/her own measurements in front of a mirror using a ruler; either with or without the assistance of another person. Since even experienced opticians have difficulty taking their own measurement in a mirror, this method is prone to pupillary measurement error(s) and its associated effects mentioned above.

Yet, another possible remote method could consist of using a software application which superimposes pictures of a frame over pictures of the individual's face without wearing a frame; the method is currently used to virtually try-on different frame designs in order to see how they look. Even if an attempt is made to get measurements from those pictures, the elevation of an optical frame on a face depends on how high the frame's nose-support seats on the person's nose, which depends on the shape of the frame's nose-support and the physiognomy of the person's nose, the desired frame's pantoscopic angle, and the height of the ears supporting the frame's temple ends.

As can be seen, there is a need for a system, method and device for measuring pupillary distance, taking into account relevant physiognomy and the desired frame of the measured individual, and so facilitating online purchases of prescription frames.

SUMMARY OF THE INVENTION

In one aspect of the present invention, a remote method for measuring a pupillary distance taking into account relevant physiognomy and a desired frame of an individual comprises: providing a calibration frame with at least one known measurement between two identified points, wherein the calibration frame is dimensioned and configured substantially the same as the desired frame, wherein the calibration frame provides two eye-frames joined at a nose-bridge, and wherein each eye-frame defines a periphery of a lens; capturing a photographed image of the calibrated frame with a co-planar imaging device at a predetermined distance from the individual's left and right eye, wherein the calibrated frame is being comfortably worn by the individual; determining a scale factor of the photographed image by comparing the at least one known measurement to an apparent distance between the two identified points captured on the photographed image; and calculating a horizontal distance between a first portion of each eye and a center of the nose-bridge by scaling each apparent horizontal distance captured on the photographed image by the scale factor of the image.

In another aspect of the present invention, a system for measuring a pupillary distance taking into account relevant physiognomy and a desired frame of an individual comprises: a calibration frame with at least one known measurement between two identified points, wherein the calibration frame is dimensioned and configured substantially the same as the desired frame, wherein the calibration frame provides two eye-frames joined at a nose-bridge, wherein each eye-frame defines a periphery of a lens, and wherein the calibration frame provides a surface of a frame front; a computer having a user interface; and a program product comprising machine-readable program code for causing, when executed, the computer to perform the following process steps: producing an electronic representation of a plurality of optical frames, each comprising at least one known measurement; prompting a user to select the desired frame from the plurality of optical frames via the user interface; instructing the user to capture and transmit a photographed image with a co-planer imaging device at a predetermined distance from the individual's left and right eye, wherein the calibrated frame is being comfortably worn by the individual; receiving the photographed image from the user; determining a scale factor of the photographed image by comparing the at least one known measurement to an apparent distance between the two identified points captured on the photographed image; and calculating a horizontal distance between a first portion of each eye and a center of the nose-bridge by scaling each apparent horizontal distance captured on the photographed image by the scale factor of the image.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a measuring system that embodies a method and a calibration frame for use in measuring pupillary distances and segment heights. The method includes an individual choosing a desired frame and then receiving a calibrated frame that substantially matches the shape and size of the desired frame. The calibrated frame also provides true measurements as well as known measurements over a vertical plane co-planar between selected points. The method includes a photographed image of the calibrated frame worn by the individual so that using the known measurements of the calibrated frame to compare to the corresponding distance measured off the photographed image, the pupillary distances and segment heights can be determined for providing prescription lens for the desired frame, including multifocal (progressive) lenses. Thereby the measuring of pupillary distances and segment heights takes into account the relevant physiognomy and the desired frame of the measured individual, and so facilitates online purchases of prescription frames.

Referring to FIGS. 1 through 4, the present invention provides a measuring system that embodies a method 60 and a calibration frame 10 for use in measuring pupillary distance, facilitating the online purchase of prescription eyeglasses.

The measuring system may include at least one computer with a user interface. The computer may include any computer including, but not limited to, a desktop, laptop, and smart device, such as, a tablet and smart phone. The computer includes a program product including a machine-readable program code for causing, when executed, the computer to perform steps. The program product may include software and/or a relevant software application which may either be loaded onto the computer or accessed by the computer. The loaded software may include an application on a smart device. The software may be accessed by the computer through the Internet. The computer may access the software through the internet, extranet, intranet, host server, internet cloud and the like.

Figure 4:
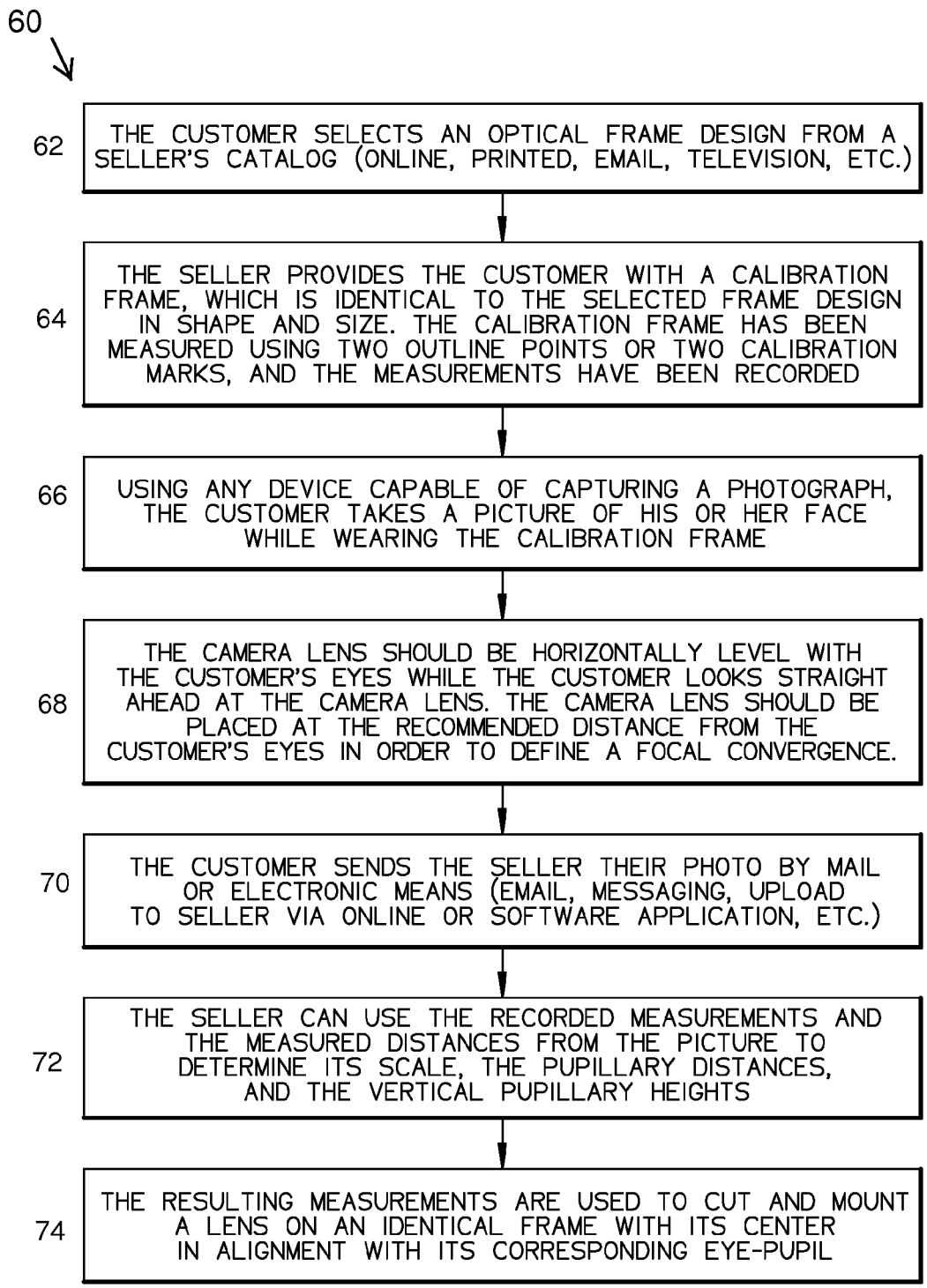
FIG. 4 is a flow chart of an exemplary embodiment of the present invention.

Referring to FIG. 4, the method 60 may include the following steps. The program product may include a relevant software application having machine-readable program code for causing, when executed, the computer to perform the process steps of method 60.

In step 62, an individual orders a desired frame. The desired frame may include any optical frame designed for housing at least one prescription lens. The order may be made by selecting from a vendor; either online, through a website, from a catalog or TV, by mail, phone or through the relevant software application. The individual must always provide his/her optical prescription to the vendor.

In step 64, the vendor or a third party supplies the calibration frame 10 to the individual. The calibration frame 10 may be a substantially similarly shaped and sized optical frame as the desired frame. The calibration frame 10 will have at least one known measurement; either (a) a true-size distance of the front of the calibration frame 10 over its vertical (co-planar) plane between selected Outline Points OP1t and OP2t, hereinafter DOPt, or (b) a true-size distance between known co-planar Calibration Marks CM1t and CM2t, hereinafter DCMt, as illustrated on FIG. 1. OP1t, OP2t, CM1t and CM2t are known as identified points. Either DOPt or DCMt may be used to determine the true-size of the calibration frame 10. The Outline Points OP1t and OP2t may be synonymous with two points on the desired frames because of the substantially similar shape and size. In certain embodiments, the calibration frame 10 could be the desired frame. The calibration frame may provide two eye-frames joined at a nose-bridge, wherein each eye-frame defines a periphery of a lens, and wherein the calibration frame provides a surface of a frame front. The periphery of the lens may be a lens aperture formed by a standard solid frame, a space occupied and accounted for in a three-piece frame, and the like.

In step 66, the individual captures a photographed image 12 by using an imagining device 28 including, but not limited to, a digital camera of a smart-phone, tablet, computer device, or electronically connected to the relevant software application. The individual is instructed to take the photographed image 12 while wearing the calibration frame 10 comfortably—as he/she intends to wear his/her eyeglasses normally. The instructions may be provided by the relevant software application.

In step 68, the instructions may include a certain predetermined distance 30 between a lens 26 of the imaging device 28 and the individual's left and right eye 32, 34. The predetermined distance 30 may define a co-planar focal convergence point. The camera lens 26 should be centered and horizontally leveled with the individual's eyes 32, 34. The instructions also may recommend looking at the camera lens 26 with the head straight (like when driving a car on a straight road) so that the predetermined distance co-planar with the individual's left and right eye.

In step 70, the individual sends the photographed image 12 to the vendor and/or third party. The photographed image 12 may be in either a physical form or electronic form sent electronically either via upload, email, messaging; or through the relevant software application.

In step 72, the vendor analyzes the photographed image 12. The analysis may be performed by the relevant software application. Already knowing DOPt or DCMt, the vendor can determine the scale factor of the image (K) from the relationship between either DOPt or DCMt of the true calibration frame 14 and its corresponding measurement from the photographed image 12.

$$K = DCMt/DCMp \text{ or } K = DOPt/DOPp$$

Pupillary Distances: With K determined, the vendor can use the photographed image 12 to determine the photographed horizontal measurements from a first portion of an individual's eye—in certain embodiments, the eye pupils 16, 18—to the center of the nose-bridge, PD(OD)p, and PD(OS) p, and then multiply by the scale factor (K) in order to calculate the pupillary distances:

PD(OD)=PD(OD)p×K

PD(OS)=PD(OS)p×K

PD=PD(OD)+PD(OS)

In essence, scaling involves comparing a known distance and an "apparent" (version of the) known distance as captured on the photographed image 12.

Figure 1:
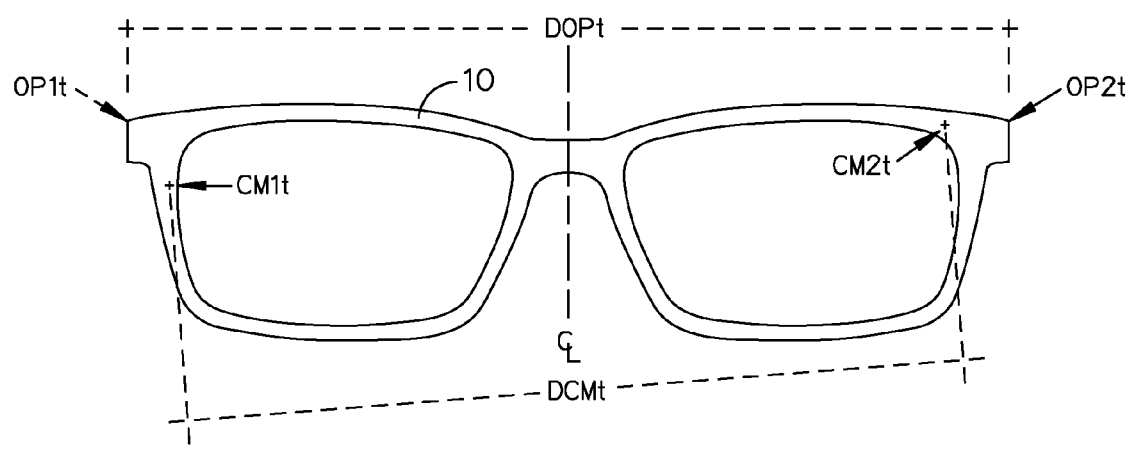
FIG. 1 is a schematic front view of an exemplary embodiment of a calibration frame of the present invention.
Figure 2:
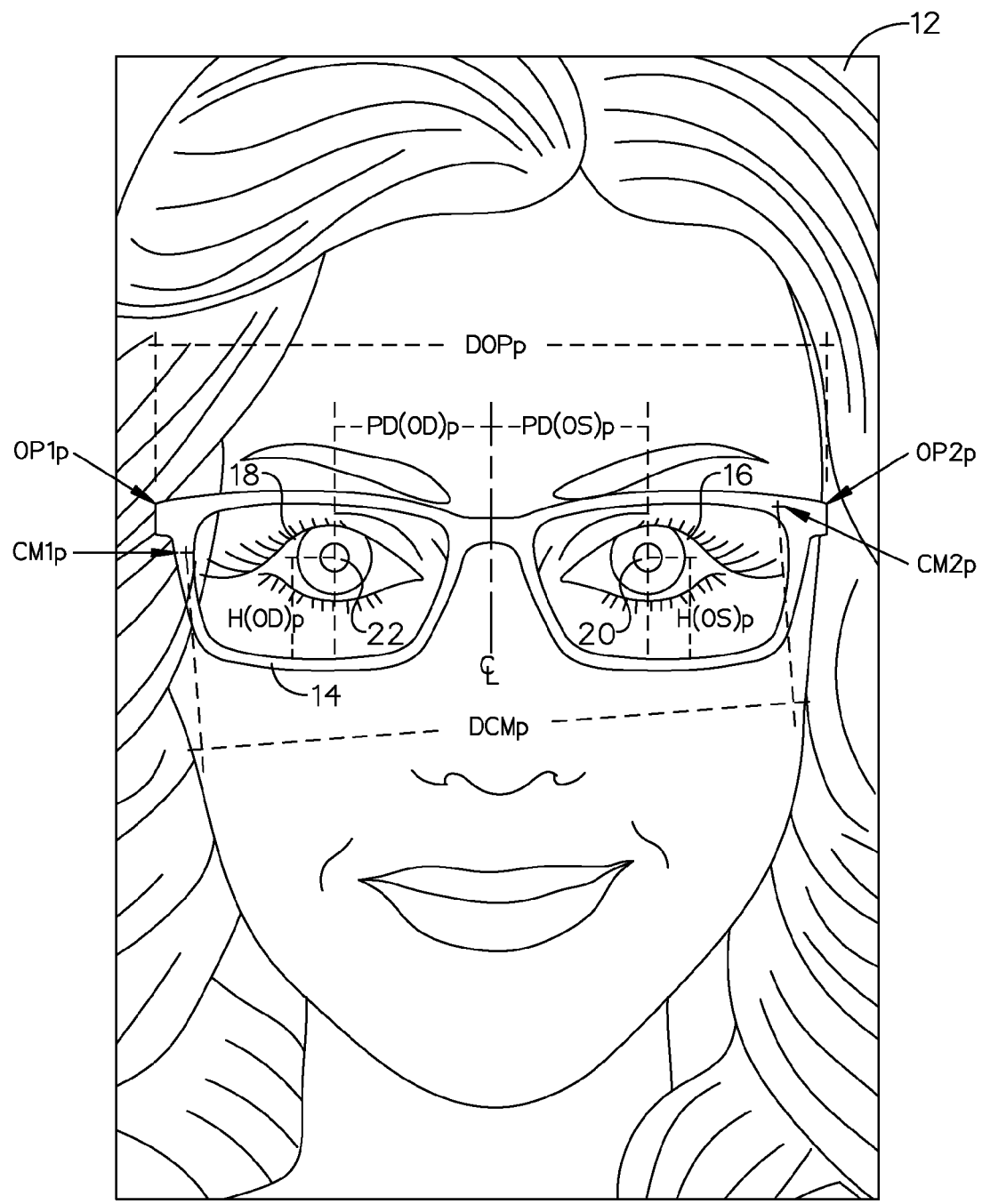
FIG. 2 is a schematic view of an exemplary embodiment of a photographed image of the present invention.
Figure 3:
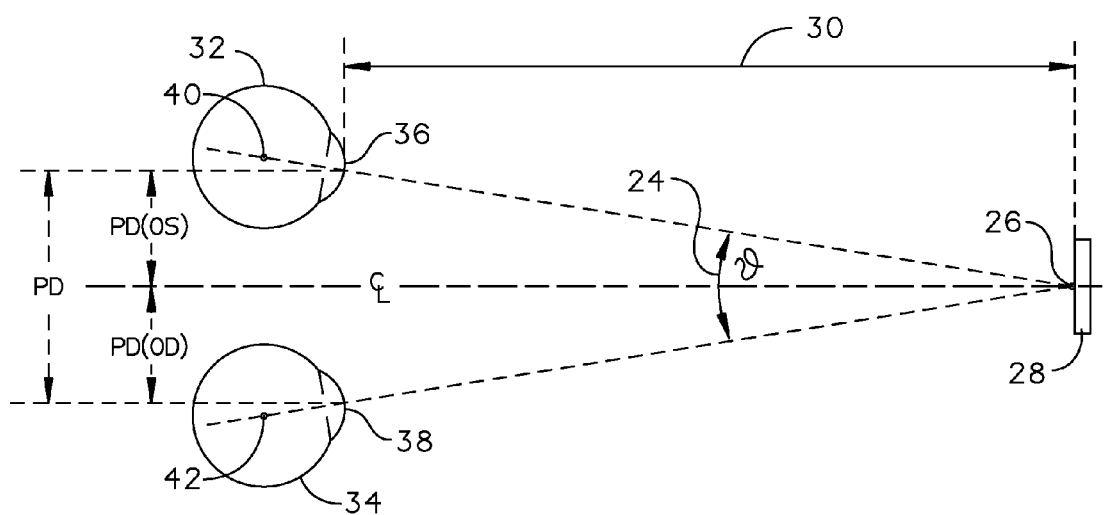
FIG. 3 is a schematic view of an exemplary embodiment of a method of measuring pupillary distance based in part on a predetermined distance.

It is understood that the prescription distance and the predetermined distance 30 between the lens 26 and the individual's left and right eye 32, 34 may be different. As long as the predetermined distance 30 is known, the horizontal measurements from the centers of the eye pupils 36, 38 to the center of the nose-bridge, PD(OD), PD(OS), and PD can be sufficiently determined for the prescription distance base on known geometry principles of a vergence angle 24 as illustrated in FIG. 3, and an understanding that most human eyes after 4 years old have roughly the same diameter-size. This similar diameter and rotational point location allows the vendor to use a vergence method and adjust the above pupillary distances in order to determine the new position of the eye pupils 36, 38 related to the rotational points 40, 42 and the vergence angle 24 corresponding to the prescription distance instead of the recommended distance, as illustrated in FIG. 3. For example, if the individual orders the desired frames for reading, the prescription distance may be 18 inches, and so if the photographed image 12 is taken from a predetermined distance 30 of thirty-six inches, then the vendor may apply the corresponding vergence angle 24 to adjust the calculations for the prescription distance of eighteen inches reading distance. On the other hand, if the individual orders desired frames for driving, the focal distance is almost infinite, therefore the vergence method allows adjusting the prescription distance for a infinite distance from the predetermined distance 30 of thirty-six inches.

Segment Heights: When ordering multifocal (progressive) eyeglasses or bi-focal eyeglasses, the photographed image 12 is used to determine the photographed vertical measurements from a second portion of each eye—in certain embodiments the eye-pupil center 20, 22, in other instances the top of the bottom eye-lid—to an downwardly and/or upwardly vertical direction to each periphery of the lens of the calibrated frame 10. Such periphery may correspond with the bottom-of-the-lens and the top-of-the-lens, respectively. In order to determine the segment height it is multiplied by the scale factor (K):

H(OD)=H(OD)p×K

H(OS)=H(OS)p×K

In step 74, the vendor uses the calculated pupillary distances and segment heights to cut and mount the prescription lenses for the desired frame in alignment with their corresponding eye pupils. And then the vendor delivers the desired frames with prescription lenses that take into account relevant physiognomy, wherein the individual may have never left their residence throughout the process. The vendor may adjust the above calculations according the lens wrap-angle and the pantoscopic tilt-angle of the calibrated frame in order to translate the pupillary distances and segment heights onto the surface of the frame front.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A remote method for measuring a pupillary distance taking into account relevant physiognomy and a desired frame of an individual, comprising:
    providing a calibration frame with at least one known measurement between two identified points, wherein the calibration frame is dimensioned and configured substantially the same as the desired frame, wherein the calibration frame provides two eye-frames joined at a nose-bridge, and wherein each eye-frame defines a periphery of a lens;
    capturing a photographed image of the calibrated frame with a co-planar imaging device at a predetermined distance from the individual's left and right eye, wherein the calibrated frame is being comfortably worn by the individual;
    determining a scale factor of the photographed image by comparing the at least one known measurement to an apparent distance between the two identified points captured on the photographed image; and
    calculating a horizontal distance between a first portion of each eye and a center of the nose-bridge by scaling each apparent horizontal distance captured on the photographed image by the scale factor of the image.

2. The remote method of claim 1, further including calculating a vertical downwardly distance and an upwardly distance between a second portion of each eye and the periphery of the corresponding lens by scaling each apparent vertical distance captured on the photographed image by the scale factor of the image.

3. The remote method of claim 2, wherein the second portion of each eye is a center of the eye-pupil.

4. The remote method of claim 2, wherein the second portion of each eye is a top of the eye's lower eye-lid.

5. The remote method of claim 1, wherein the first portion each eye is a center of the eye-pupil.

6. The remote method of claim 1, further including remotely selecting the desired frame from a vendor, wherein the vendor provides the calibration frame to the individual.

7. The remote method of claim 6, further providing predetermined instructions provided by the vendor, wherein the predetermined instructions comprise the predetermined distance.

8. The remote method of claim 7, further including accounting for when the predetermine distance differs from the instructed predetermined distance by using a vergence angle and relevant eye-pupil rotational points.

9. The remote method of claim 1, wherein the two identified points are synonymous with the desired frames.

10. The remote method of claim 1, wherein the calibration frame is the desired frame.

11. The remote method of claim 1, wherein the two identified points of a known measurement are calibration marks disposed on the calibration frame.

12. A system for measuring a pupillary distance taking into account relevant physiognomy and a desired frame of an individual, comprising:
 a calibration frame with at least one known measurement between two identified points, wherein the calibration frame is dimensioned and configured substantially the same as the desired frame, wherein the calibration frame provides two eye-frames joined at a nose-bridge, wherein each eye-frame defines a periphery of a lens, and wherein the calibration frame provides a surface of a frame front;
 a computer having a user interface; and
 a program product comprising machine-readable program code for causing, when executed, the computer to perform the following process steps:
  producing an electronic representation of a plurality of optical frames, each comprising at least one known measurement;
  prompting a user to select the desired frame from the plurality of optical frames via the user interface;
  instructing the user to capture and transmit a photographed image with a co-planer imaging device at a predetermined distance from the individual's left and right eye, wherein the calibrated frame is being comfortably worn by the individual;
  receiving the photographed image from the user;
  determining a scale factor of the photographed image by comparing the at least one known measurement to an apparent distance between the two identified points captured on the photographed image; and
  calculating a horizontal distance between a first portion of each eye and a center of the nose-bridge by scaling each apparent horizontal distance captured on the photographed image by the scale factor of the image.

13. The system of claim 12, further including calculating a vertical downwardly distance and an upwardly distance between a second portion of each eye and the periphery of the corresponding lens by scaling each apparent vertical distance captured on the photographed image by the scale factor of the image.

14. The system of claim 13, further including providing the vendor the calculated horizontal distances and the calculated vertical downwardly and upwardly distances for cutting multi-focal prescription lenses for the desired frame.

15. The system of claim 14, further including translating the calculated vertical downwardly and upwardly distances over the surface of the frame front.

16. The system of claim 12, wherein the imaging device is electronically connected to the program product.

17. The system of claim 12, further including remotely selecting the desired frame from a vendor, wherein the vendor provides the calibration frame to the individual.

18. The system of claim 17, wherein the calibration frame is a physical representation of the desired frame.

19. The system of claim 18, wherein the calibration frame comprises two calibration marks of a known measurement.

20. The system of claim 15, further including prompting the user as to whether the desired frame is for reading, desk computer work, or seeing far.

21. The system of claim 20, further including accounting for when the predetermine distance differs from the instructed predetermined distance by using a vergence angle and relevant eye-pupil rotational points.

22. The system of claim 12, further including providing the vendor the calculated horizontal distances for cutting prescription lenses for the desired frame.

23. The system of claim 22, further including translating the calculated horizontal distances over the surface of the frame front.

* * * * *